United States Patent [19]

Sicardi

[11] 4,382,941
[45] May 10, 1983

[54] BISHYDRAZIDE QUATERNARY SALTS AND PHARMACEUTICAL COMPOSITIONS THEREOF

[76] Inventor: Susana M. Sicardi, Cereti 2515, 8th Floor, Bs. As., 1431 Buenos Aires, Argentina

[21] Appl. No.: 210,585

[22] Filed: Nov. 26, 1980

[51] Int. Cl.³ .................... A61K 31/44; C07D 213/02
[52] U.S. Cl. ..................................... 424/263; 546/332
[58] Field of Search ................ 546/332; 564/148, 149, 564/150, 151; 424/263

[56] References Cited

U.S. PATENT DOCUMENTS

| | | | |
|---|---|---|---|
| 2,045,132 | 6/1936 | Girard et al. | 546/332 |
| 2,729,644 | 1/1956 | Klopping | 546/332 |
| 2,729,646 | 1/1956 | Klopping | 546/332 |
| 2,763,684 | 9/1956 | Beman | 564/150 |
| 2,767,173 | 10/1956 | Katz | 564/150 |
| 3,884,874 | 5/1975 | Rosenberger et al. | 564/150 |

Primary Examiner—Robert T. Bond
Attorney, Agent, or Firm—Fleit, Jacobson & Cohn

[57] ABSTRACT

The present invention relates to novel bishydrazide quaternary salts, useful as surfactants and antibacterial agents. The novel bishydrazide quaternary salts correspond to the general formula

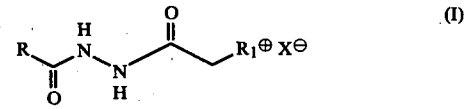

wherein
R=($C_9$–$C_{19}$)alkyl, ($C_{13}$–$C_{19}$)alkenyl, unsubstituted and substituted aryl;
$X^-$ is an anion, and
$R_1^+$ is a

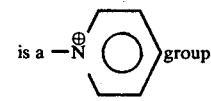

group The present invention also relates to processes of preparing the compounds of formula (I) and antibacterial compositions containing them.

3 Claims, No Drawings

BISHYDRAZIDE QUATERNARY SALTS AND PHARMACEUTICAL COMPOSITIONS THEREOF

BACKGROUND OF THE INVENTION

1. Field of the Invention

The present invention relates to novel bishydrazide quaternary salts, useful as surfactants and antibacterial agents, to process of preparing such novel compounds and to compositions for antibacterial use containing them.

2. Description of the Prior Art

Labile quaternary ammonium salts of the type R-COOCHR$_1$-N$^\oplus$,X$^\ominus$ (wherein R=straight or branched long alkyl or aralkyl, R$_1$=H, alkyl, aryl, etc. and X=Cl, Br, I, etc.) were disclosed by U.S. Pat. No. 3,984,711. These "soft" quaternary salts are isosteric analogues of known "hard" quaternary surfactants, and are characterized by predictable and controllable cleavage (metabolism) to non toxic components. The hydrolytic sensivity of the ester portion also affects their activity in vivo. The compounds of formula (I) in front to the above known compounds were modified by the introduction of an amidocarbamoyl group which provides a higher metabolic resistance.

SUMMARY OF THE INVENTION

The present invention relates to novel bishydrazide quaternary salts of the formula (I) which avoid the systematic toxicity of the quaternary surface-active agents. The compounds of this invention possess surfactant characteristics and display in vitro antimicrobial activity against representative bacteriae and fungi. The highest activity is shown against gram(+) bacteriae such as *Staphylococcus aureus* and *Streptococcus pyogenes*.

The compounds of formula (I) can be obtained by the following methods:

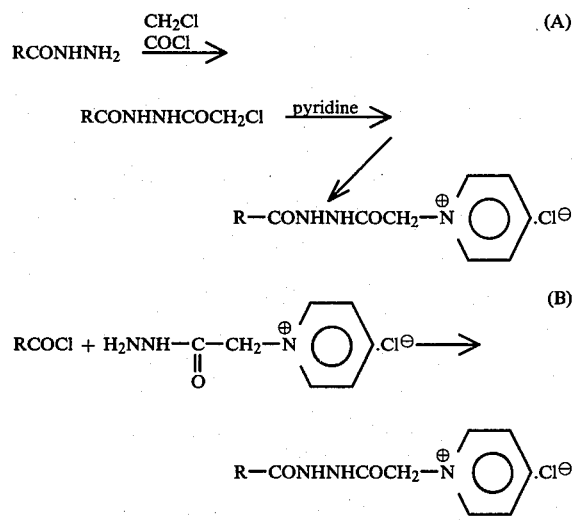

DETAILED DESCRIPTION OF THE PREFERRED EMBODIMENTS

The compounds of formula (I) can be obtained in accordance with the above method (A) by direct quaternization of the appropriated N'-(chloroacetyl)alkanoic or benzoic acid hydrazide in dry pyridine in excess, and heating in water bath during 15–30 min. The compound crystallizes upon cooling.

The N'-(chloroacetyl)alkanoic or benzoic acid hydrazide useful as starting material is obtained by adding dropwise 0.01 mole of chloroacetyl chloride to a solution of 0.01 mole of the corresponding hydrazide in 10 ml of dry dioxane. Stirring should be continued during 4 hours at room temperature, and then the precipitate should be filtered off, washed with dioxane and dried.

In accordance with the above method (B), equimolecular amounts of the corresponding acyl chloride and pyridiniumacetohydrazide chloride should be mixed and heated at a temperature range of 50°–70° C. for 2–5 hours. Upon the mixture cools at room temperature anhydrous ether should be added and the solid isolated by filtration.

EXAMPLE 1

Preparation of N'-(pyridiniumacetyl)decanoic acid hydrazide chloride

A solution of 8.0 g (0.03 mole) of N-(chloroacetyl)-decanoic acid hydrazide and 34.3 g (0.43 mole) of dry pyridine was heated in a water bath at 60° C. for 15 min. Upon cooling of the solution, there crystallized N'-(pyridiniumacetyl)decanoic acid hydrazide chloride. The solid was removed by filtration and dried in vacuo. Recrystallization from EtOH—AcOet gave 10.1 g (97%) of the final product. NMR (D$_2$O) 0.85 (br,3, methyl protons), 1.25 (5,14, methylene protons), 2.35 (6,2 methylene carbonyl protons), 5.65 (5,1,N-methylene protons), 8.15–8.8 ppm (m,s, aromatic protons); melting point 201°–202° C.

EXAMPLE 2

Preparation of N'-chloroacetyl-(2-benzoylthio)-benzohydrazide

To a solution of 3 g (0.01 mole) of 5-benzylbenzohydrazide in 10 ml of dry dioxane 1 ml (0.01 mole) of chloroacetyl chloride was added dropwise with stirring. Stirring was continued for 2–3 hours at room temperature, and the solution was cooled, precipitating the crude product. Recrystallization from EtOH gave 80.6% of the final product; m.p. 143°–144° C.; IR (BrK)=3200–3030–1650–1600–1540–780 cm$^{-1}$.

EXAMPLE 3

Preparation of 1-[(2-benzylthio)-benzamidocarbamoyl-methyl]-pyridinium 3.34 g (0.01 mole) of N'-chloroacetyl-(2-benzylthio)-benzohydrazide were added to 10 ml of dry pyridine. The solution was heated at 50° C. in a water bath for 15–30 min. After a few minutes, the pyridinium salt crystallized and the solid was removed by filtration, dried in vacuo, and recrystallized from MeOH—AcOEt; m.p. 198°–199° C. (dec.). IR (BrK): 3120–3050–1700–1660–1640–1540–1550 cm$^{-1}$.

Proceeding in a similar manner there were obtained the following compounds:

TABLE I

Physical Properties of N'—(Pyridinioacetyl)alkanoic and - benzoic Acid Hydrazide Chloride Salts

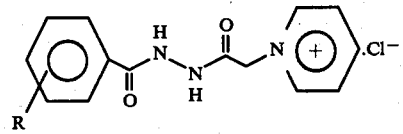

1-9

| N°[a] | R | m.p. °C.[b] | Yield %[c] | δ, dyn/cm, ±SD[d] |
|---|---|---|---|---|
| 1 | $C_3H_7$ | 172–173 | 80.3 | 64.42 ± 0.01 |
| 2 | $C_4H_9$ | 180–181 | 85.1 | 64.12 ± 0.01 |
| 3 | $C_5H_{11}$ | 190–191 | 79.0 | 62.82 ± 0.02 |
| 4 | $C_7H_{15}$ | 199–200 | 95.2 | 51.12 ± 0.01 |
| 5 | $C_{11}H_{23}$ | 191–192 | 90.7 | 43.42 ± 0.02 |
| 6 | $C_{13}H_{27}$ | 189–190 | 90.9 | 41.51 ± 0.01 |
| 7 | $C_{15}H_{31}$ | 182–183 | 82.3 | 39.91 ± 0.02 |
| 8 | $C_{17}H_{35}$ | 180–181 | 89.9 | 42.52 ± 0.01 |
| 9 | $\Delta^9$-cis-$C_{17}H_{33}$ | 180–181 | 92.78 | 40.50 ± 0.01 |

| N° | R | m.p. °C.[b] | Yield %[c] | δ, dyn/cm, ±SD[d] |
|---|---|---|---|---|
| 10 | H | 275–276 | 75.2 | 62.38 ± 0.01 |
| 11 | o-OH | 257–258 | 89.1 | 63.25 ± 0.01 |
| 12 | o-$SCH_2$Phe | 198–199 | 80.6 | 63.66 ± 0.01 |
| 13 | o-$SCH_2CH=CH_2$ | 193–194 | 98.0 | 62.42 ± 0.02 |
| 14 | o-$SOCH_2$Phe | 227–228[e] | 95.2 | 53.26 ± 0.02 |
| 15 | o-$SO_2CH_2$Phe | 240–241 | 82.0 | 51.17 ± 0.01 |
| 16 | o-$OCH_2$Phe | 224–225 | 82.0 | 65.46 ± 0.01 |
| 17 | o-Cl | 212–213[e] | 85.0 | 64.99 ± 0.02 |
| 18 | m-$NO_2$ | 256–257 | 80.6 | 61.22 ± 0.01 |
| 19 | p-$NO_2$ | 277–278 | 76.5 | 58.17 ± 0.01 |
|  | o-SH | unstable |  |  |

[a] All were analyzed for C, H, and N, and results were within ± 0.03% of theory.
[b] After recrystallization from ethanol-ethyl acetate, with dec.
[c] Yield of the recrystallized product in the last reaction step.
[d] Surface tension of 0.1% aqueous solution at 22 ± 1° C.
[e] Hygroscopic.

Minimal Inhibitory Concentration (MIC), mcg/ml

In vitro antimicrobial activity was determined using the autotitration method [Goss W. A. and E. B. Cimijotti, Appl. Microbiol., 1968, 16, 1414].

The bacteriae were inoculated into tryptose phosphate broth (Difco) and incubated at 37° C. for 18–20 hours. The fungi were inoculated into protease peptone N° 3 maltose and incubated at 23° C. for 3–5 days. Absence of growth (turbidity) was indicative of the activity of the drug being evaluated. The lowest level of drug which completely inhibited the development of growth is considered the MIC. Results are summarized as MIC (mcg/ml):

| Organism | I | II | III | IV | V |
|---|---|---|---|---|---|
| S. aureus Smith | 31.3 | 7.8 | 1.95 | 15.6 | 7.8 |
| E. coli Vogel. | 125 | 15.6 | 15.6 | 31.3 | 31.3 |
| K. pneumonia 39645 | 250 | 15.6 | 31.3 | 31.3 | 31.3 |
| P. vulgaris 9920 | 250 | 31.3 | 31.3 | 31.3 | 31.3 |
| P. mirabilis MGH-1 | 500 | 31.3 | 31.3 | 31.3 | 31.3 |
| Ps. aeruginosa MGH-2 | 125 | 31.3 | 15.6 | 15.6 | 15.6 |
| S. pyogenes C-203 | 15.6 | 7.8 | 3.9 | 0.5 | 0.5 |
| C. albicans 10.231 | 62.5 | 15.6 | 7.8 | 7.8 | 7.8 |
| As. niger 16.404 | 62.5 | 15.6 | 15.6 | 15.6 | 15.6 |
| T. mentagrophytes 9129 | 62.5 | 15.6 | 15.6 | 7.8 | 7.8 |

Application

The compounds of the present invention are proposed as surfactant and antimicrobial agents.

Particularly the final compound of Example 1 and compound 4, due to their high selective activity against S. pyogenes and low toxicity, are potential drugs which can be used as alternative of penicillin in the treatment of rheumatic fever.

Chagas' Disease

A screening procedure for assessment of schizotrypanocidal activity of candidate compounds against Trypanosoma cruzi infections in mice:

The test system uses mortality of ICR/HA mice during the acute phase of infection as an index of drug activity against the trypomastigote and amastigote forms of T. cruzi.

Male inbred ICR/HA mice are given a single subcutaneous injection of the test compounds suspended in refined peanut oil or aqueous 0.5% hydroxyethylcellulose—0.1% Tween (HEC).

Each compound is tested at doses of 640–160 and 40 mg/kg. Negative controls receive an injection of the vehicle alone. Three hours after drug administration, treated and control animals are challenged intraperitoneally with aproximately 8,000 trypomastigotes in saline-diluted blood drawn from donor mice infected three weeks previously with T. cruzi trypomastigotes (Y-strain).

Mortality over the next 40 days is used as an index of compound schizotrypanocidal activity. The Y-strain consistently produces 100% mortality in untreated mice in approximately three weeks, all deaths falling within a narrow time range (11–15 days).

Relative activity of compounds are assessed by comparing the life space of treated animals to that of negative controls. Compounds are classified as active, slightly active, or inactive. An active compound is one which produces a life space at least 50% greater than that of the controls. A slightly active compound produces a 20 to 49.9% increase in longevity. A compound producing less than 19.9% increase in life space is considered to be inactive.

Assays on the "Experimental Chagas' Disease" effected by the Walter Reed Army Institute of Research (U.S.A.)

| R | W.R[1] | Dose[2] | Daily Mortality[3] | $T_c^4$ | $T_T^5$ | $T_T - T_c^6$ |
|---|---|---|---|---|---|---|
| $C_{11}H_{23}$— | BH 89 269 | 40 | 9/1;10/1;11/1;12/2 | 13.2 | 10.8 | −2.4 |
|  |  | 140 | 10/1;11/4 | 13.2 | 10.8 | −2.4 |

-continued
Assays on the "Experimental Chagas' Disease" effected by the Walter Reed Army Institute of Research (U.S.A.)

| R | W.R[1] | Dose[2] | Daily Mortality[3] | $T_c$[4] | $T_T$[5] | $T_T - T_c$[6] |
|---|---|---|---|---|---|---|
| $C_{13}H_{27}-$ | BH 89 278 | 640 | 0/2; 1/3 (toxic) | 13.2 | 0 | −13.2 |
| | | 40 | 9/2; 11/3 | 10.4 | 10.2 | −0.2 |
| | | 140 | 6/1;9/1;11/2;13/1 | 10.4 | 11.0 | 0.6 |
| $\Delta^9$-cis-$C_{17}H_{33}-$ | BJ 30 752 | 640 | 0/2;11/2;13/1 (toxic) | 10.4 | 11.7 | 1.3 |
| | | 40 | 11/3;12/1;13/1 | 10.4 | 11.6 | 1.2 |
| | | 140 | 11/5 | 10.4 | 11.0 | 0.6 |
| 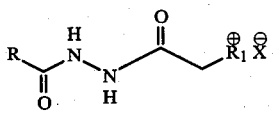 (OH) | BH 89 250 | 640 | 10/2;11/2;13/1 | 10.4 | 11.0 | 0.6 |
| | | 40 | 11/2;12/1;13/2 | 13.2 | 12.0 | −1.2 |
| | | 140 | 9/1;13/2;17/1;19/1;20/1 | 13.2 | 15.6 | 2.4 |
| | | 640 | 11/4;12/1 | 13.2 | 11.2 | −2.0 |
| (SCH₂Phe) * | BH 89 241 | 40 | 10/1;11/4 | 10.8 | 10.8 | 0 |
| | | 140 | 10/1;11/1;12/1;16/1;19/1 | 10.8 | 13.6 | 2.8 |
| | | 640 | 1/1;10/3;11/1 | 10.8 | 10.3 | 0.5 |

The remaining compounds are being assayed.
[1] Identification Code of the Walter Reed Army Institute of Research
[2] Subcutaneously-administered doses, in mg/kg per day
[3] Each fraction indicates the number of days after injection and the denominator shows the number of deaths produced on that day
[4] Survival time of the control animals (5 mice)
[5] Survival time of the treated animals (5 mice)
[6] Changes in survival time ($T_T - T_c$)
* light trypanocidal activity against *T. cruzi*

What I claim is:

1. A compound of the formula

wherein
R is $(C_9-C_{19})$-alkyl, $(C_{13}-C_{19})$-alkenyl, phenyl or phenyl substituted by OH, SCH₂Phe, SCH₂CH=CH₂, SOCH₂Phe, SO₂CH₂Phe, OCH₂Phe, Cl, NO₂, or SH;
X is a halogen anion, and
$R_1$ is pyridinium.

2. A compounds in accordance with claim 1, wherein R is $(C_9-C_{19})$-alkyl or unsubstituted phenyl or phenyl substituted with hydroxy, halogen or nitro.

3. A compositions for antibacterial use containing an effective amount of a compound of the formula (I) of claim 1 together with a suitable carrier.

* * * * *